United States Patent [19]

Davis et al.

[11] 4,179,337

[45] Dec. 18, 1979

[54] NON-IMMUNOGENIC POLYPEPTIDES

[76] Inventors: Frank F. Davis, 19 Farmingdale Rd., East Brunswick, N.J. 08816; Theodorus Van Es, 313 Overbrook Rd., Piscataway, N.J. 08854; Nicholas C. Palczuk, 45 W. Franklin St., Bound Brook, N.J. 08805

[21] Appl. No.: 819,831

[22] Filed: Jul. 28, 1977

Related U.S. Application Data

[63] Continuation-in-part of Ser. No. 596,931, Jul. 17, 1975, abandoned, which is a continuation-in-part of Ser. No. 381,191, Jul. 20, 1973, abandoned.

[51] Int. Cl.$^2$ .................... C07G 7/00; C07G 7/02; A61K 37/26; A61K 37/48
[52] U.S. Cl. .................. 435/181; 260/112.5 R; 260/112.7; 424/78; 424/94; 424/177; 424/178; 435/180
[58] Field of Search ............... 195/63, 68, DIG. 11; 424/94, 177, 178, 78; 260/112.5, 112 R, 6, 8, 112.7

[56] References Cited

U.S. PATENT DOCUMENTS

| | | | |
|---|---|---|---|
| 3,607,653 | 9/1971 | Ziffer et al. | 195/63 |
| 3,619,371 | 11/1971 | Crook et al. | 195/63 |
| 3,639,213 | 2/1972 | Ginger et al. | 195/63 |
| 3,645,852 | 2/1972 | Axon et al. | 195/68 |
| 3,788,948 | 1/1974 | Kagedal et al. | 195/68 |
| 3,959,080 | 5/1976 | Orth et al. | 195/68 X |
| 4,002,531 | 1/1977 | Royer | 195/DIG. 11 |
| 4,055,635 | 10/1977 | Green et al. | 195/DIG. 11 |

*Primary Examiner*—David M. Naff
*Attorney, Agent, or Firm*—Omri M. Behr

[57] ABSTRACT

Polypeptides such as enzymes and insulin are coupled to polyethylene glycol or polypropylene glycol having a molecular weight of 500 to 20,000 daltons to provide a physiologically active non-immunogenic water soluble polypeptide composition. The polyethylene glycol or polypropylene glycol protect the polypeptide from loss of activity and the composition can be injected into the mammalian circulatory system with substantially no immunogenic response.

27 Claims, No Drawings

NON-IMMUNOGENIC POLYPEPTIDES

RELATED APPLICATIONS

This application is a continuation-in-part of our co-pending application, Ser. No. 596,931 filed July 17, 1975, which, in turn, is a continuation-in-part of our then co-pending application, Ser. No. 381,191, filed July 20, 1973, both now abandoned.

BACKGROUND OF THE INVENTION

1. Field of the Invention
Non-immunogenic polypeptides.

2. Description of the Prior Art

The use of polypeptides in circulatory systems for the purpose of engendering a particular physiological response is well known in the medicinal arts. Among the best known polypeptides utilized for this purpose is insulin which is used in the treatment of diabetes. Another group of polypeptides to which great therapeutic potential has been attributed are enzymes of the various classes. The principal factor which has severely limited the use in therapeutics of polypeptides in particular, enzymes, has been the fact that most of these compounds elicit an immunogenic response in the circulatory system. This response being the production of antibodies to the polypeptides by the circulatory system into which they are injected. This effect has one or both of two secondary consequences. The first being the destruction of polypeptides by the antibodies so called forth, or, the second more seriously, the appearance of an allergic response.

The destruction of the polypeptide by the antibodies is believed to be responsible for the rather low residence time of insulin in the human circulatory system, hence, persons afflicted with diabetes are forced to inject themselves fairly frequently with fresh doses of insulin. In the case of enzymes not only is there a problem of destruction of the polypeptide and the subsequent negation of its physiological activity but also the most undesired elicitation of an allergic reaction.

If it were found possible to so modify polypeptides that their desired physiological activity was maintained totally or at least in substantial proportion and at the same time no immunogenic response was generated within the circulatory system, then it would be possible to utilize these most valuable compounds in the mammalian circulatory system without the aforementioned disadvantages and in the far smaller amounts than has heretofore been possible.

The problems set forth hereinabove are well recognized and various approaches have been taken in attempts to solve them. The attachment of enzymes to insoluble supports has been the subject of a great deal of work. Reviews dealing with this subject will be found in Silman and Katchalski, Ann. Rev. Biochem., 35, 873 (1966), and Goldstein, Fermentation Advances, Academic Press, New York (1969) page 391. This approach however while of academic interest does not provide injectable long-life polypeptides. Another approach which has been taken to provide polypeptides of lengthened in vivo life has been the micro incapsulation of enzymes which has been discussed in numerous articles by Chang and co-workers, namely, Science, 146, 524 (1964); Trans. Am. Soc., 12, 13 (1966); Nature, 218, 243 (1968); Can. J. Physiol. Pharmacol., 47, 1043 (1969); Canad. J. Physiol. Pharmacol., 45, 705 (1967). A further approach lay in the heat stabilization of enzymes by attaching carboxy methylcellulose to an enzyme such as Trypsin (Mitz and Summaria, Nature, 189, 576 (1961) and the attachment of proteases to hydrophilic carriers (Brummer, et al, Eur. J. Biochem., 25, 129 (1972). These approaches however do not provide the polypeptides in a soluble form which is the most desirable for injection and dosage control of injectable materials. A further approach has been the attachment of synthetic polymers to polypeptidal proteins. A review of this work will be found in Sela, "Advances in Immunology", 5, 30, (1966) Academic Press, New York. In this work, it has been shown that while homopolymers of amino acids are nearly all non-immunogenic, when these polymers are attached to immunogenic proteins the immunogenic activity is not masked and antibodies are produced in test circulatory systems. For example, while polyglycine itself is non-immunogenic, when attached to a protein that conjugated protein becomes a hapten. Similarly while dextran itself is slightly immunogenic when coupled to insulin the insulin-dextran coupled material is believed to become substantially immunogenic.

SUMMARY OF THE INVENTION

There are provided by this invention peptides and polypeptides coupled to polymers which are substantially non-immunogenic and retain a substantial proportion of the desired physiological activity of the base polypeptide.

In the process of this invention a substantially straight chain polymer is modified, suitably at one end thereof, either by the alteration of the terminal group or by the addition thereto of a coupling group having activity vis a vis a polypeptide and reacting said activated polymer with the polypeptide. The protected polypeptides of the present invention are injectable in aqueous solution into the mammalian circulatory system or intramuscular and call forth substantially no immunogenic response.

DESCRIPTION OF THE PREFERRED EMBODIMENTS

The polymers utilized for protection purposes in the procedures of the present invention possess a substantially linear ethereal or carbon carbon backbone. It has been found that utilizing branch chain polymers will give rise to substances which do generate an immunogenic response. Nevertheless a certain amount of substitution in the backbone is permissible. For example, the backbone may be substituted by alkyl groups or alkoxy groups provided that said alkyl or alkoxy groups contain less than 5, preferably 2 or less carbon atoms. Among the polymers of choice may be mentioned polyethylene glycol, and polypropylene glycol, of these polyethylene glycol is particularly preferred.

It is also preferred to operate in a polymer chain length area of between 500 and 20,000 daltons, about 750 to 5,000 daltons being especially preferred.

Several modes of coupling the polymer with the polypeptide are available and will be discussed in further detail hereinbelow. It should be borne in mind however that the portions of any given polypeptide moiety which has a desirable physiological action may vary from peptide to peptide. Thus, in certain enzymes one or two amino acid residues may be principally responsible for this desirable physiological activity. In choosing a coupling agent to couple a polymer to the polypeptide it would be desirable to utilize coupling agents which do not have an affinity for these particular active moieties. While this is a desirable goal it is not always possible to comply absolutely with it. It is therefore necessary in individual cases to effect a compromise, that is to say, sacrifice a certain amount of activity maintenance for the granting of a substantial amount of non-immunogenicity. The final results obtained will depend not only on the coupling agent used but also the proportions of reagents and molecular weight of the polymer. Nevertheless, it has been found practical with most polypeptides to utilize between 10 and 100, suitably between 15 and 50 moles of polymer per mole of polypeptide. Utilizing these proportions it has been found that at least 15% of the physiological activity has been maintained. While the scope of the invention should not be considered limited thereto, it is generally preferred to provide conditions wherein at least 40% of the physiological activity is preserved.

The procedures of the present invention are generally applicable to peptides and polypeptides, that are of particular interest in applications involving enzymes and peptide hormones. Among the enzyme categories which may be used may be mentioned:

Oxidoreductases such as: Urate: oxygen oxidoreductase (1.7.3.3; "uricase"); Hydrogen-peroxide: hydrogen-peroxide oxidoreductase (1.11.1.6; "catalase"); Cholesterol, reduced - NADP: oxygen oxidoreductase (20-β-hydroxylating) (1.14.1.9; "Cholesterol 20-hydroxylase").

Transferases such as: UDP glucuronate glucuronyl-transferase (acceptor unspecific) (2.4.1.17; "UDP glucuronyltransferase"); UDP glucose: α-D-Galactose-1-phosphate uridylyltransferase 2.7.7.12).

Hydrolases such as: Mucopeptide N-acetylmuramyl-hydrolase (3.2.1.17; lysozyme); Trypsin (3.4.4.4); L-Asparagine aminohydrolase (3.5.1.1; "Asparaginase").

Lyases such as: Fructose-1,6-diphosphate D-glyceraldehyde-3-phosphate-lyase (4.1.2.12: "aldolase").

Isomerases such as: D-Xylose ketol-isomerase (5.3.1.5; xylose isomerase) and

Ligases such as: L-Citrulline: L-aspartate ligase (AMP) (6.3.4.5).

Among the peptide hormones may be mentioned are insulin, ACTH, Glucagon, Somatostatin, Somatotropin, Thymosin, Parathyroid hormone, Pigmentary hormones, Somatomedin, Etythropoietin, Luteinizing hormone, Chorionic Gonadotropin, Hypothalmic releasing factors, Antidiuretic hormones, Thyroid stimulating hormone and Prolactin.

The resultant products from these two categories of coupling are exemplified hereinbelow. Polyethylene glycol (hereinafter PEG) has been selected as the preferred embodiment of the polymer used, but has been employed solely for purposes of illustration and not limitation. Similar products would be obtained with any of the other polymers utilized in the scope of the present invention. PEG—O—$_x$ is the terminal portion of a polymer chain where O is the residual oxygen from the terminal hydroxyl, similwarly in PEG-NH,N is the residual terminal nitrogen of the amino group replacing the terminal hydrogen. Again with respect to the peptide moiety which is representationally illustrated below as

is the residual nitrogen of a labile primary amino moiety on the peptide, and in

is the carbon atom of a labile COOH group. While the foregoing exemplification shows the peptide moiety being coupled through an amino group, and this is believed to be the most likely coupling point, the invention is not limited thereto as other labile moieties, i.e. thial might also provide a coupling locus.

In the first category there may be mentioned as a suitable coupling group cyanuric chloride or fluoride. In this procedure polyethylene glycol (hereinafter PEG) is taken up in a suitable reaction inert solvent such as a hydrocarbon solvent suitably anhydrous benzene containing a small amount of a weak base such as sodium carbonate, and cyanuric chloride added thereto. The reaction mixture is then quenched with water, insoluble material removed, followed by removal of the solvent, suitably under reduced pressure to yield 2-PEG-4-hydroxy-6-chloro-1,3,5-triazine.

The thus produced activated polymers are then reacted with a solution of polypeptide in a suitable buffer. After reaction is complete the unreacted activated polymer is removed, suitably by contacting with an gel permeation resin such as Sephadex G-50 and the protected polypeptide removed and purified in the usual manner. Since these products are to be considered as polypeptides-care must be taken during the purification procedure that they not be denatured. Therefore, it is desirable either to permit them to remain in buffered aqueous solution or, if it is deemed essential, to isolate them in the solid state that such isolation be carried out by the recognized procedure such as lyophilization of the protected peptide.

Thus, as the partial structure, say,

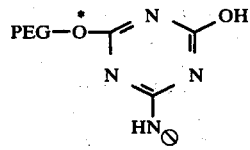

Another suitable terminal group is the acyl azide terminal group. In the production thereof, the terminal hydroxyl of the polymer is reacted with chloroacetic anhydride and subsequently with diazomethane to yield the methyl ester of the carbomethoxy ether. Treatment with hydrazine gives the corresponding hydrazide which on treatment with nitrous acid yields the desired acyl azide.

The azido moiety of the thus produced acyl azide will react with, say, a labile amino moiety on the peptide to provide a protected peptide of the partial structure, say,

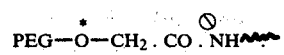

In place of treatment with hydrazine there may be utilized N-ethoxy carbonyl-2-ethoxy 1,2-dihydroquinoline, EEDQ. The quinoline is eliminated to give the corresponding mixed carbonic anhydride which is a "disappearing" coupling group having as the effective coupling moiety, say, the O-PEG-methyl carbonyl moiety which attaches itself to free amino groups on the polypeptide, to provide a resulting product which has the same structure as that shown to be obtained in the preceeding paragraph hereof.

The succinate group may also be used as a coupling moiety. In this modification the glycol, for example, PEG or PPG, is taken up in a suitable reaction inert solvent in the presence of a mild base, such as sodium bicarbonate and treated with a dihalosuccinic anhydride such as dibromosuccinic anhydride. The thus produced, say, PEG-dihalo succinate is then available for reaction with a polypeptide yielding a protected peptide of partial structure

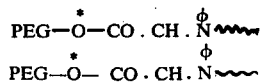

The p-diazo benzyl group is a suitable coupling agent. P-nitrobenzyl chloride is reacted with the glycol, suitably PEG in the presence of base, suitably an alkali in an anhydrous non-hydroxylic medium, preferably under reflux to produce the corresponding PEG p-nitrobenzyl ether which is then reduced to the corresponding amine by catalytic hydrogenation followed by diazotization to yield the desired O-PEG-p-diazonium benzyl ether which is then available for coupling with the polypeptide, to yield a protected peptide having the partial structure

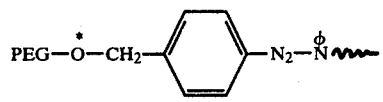

The 3-(p-diazophenyloxy)-2-hydroxy propyloxy group is prepared by treating the glycol in the presence of alkali at moderately elevated temperatures in an aqueous medium with glycidyl p-nitrophenyl ether to form the corresponding 3-(p-nitrophenyloxy) 2-hydroxypropyl ether of PEG. The nitro group is reduced to the corresponding amino group, preferably by aqueous titanous chloride in dilute mineral acid and the resulting amine diazotized to provide the diazonium ether which may then be reacted with the polypeptide, to yield a protected peptide having the partial structure

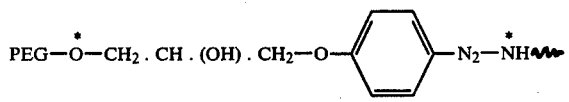

The 1-glycydoxy-4-(2'-hydroxy-3'-propyl) butane group is attached to the terminal oxygen group of the glycol and is reacted with free amino group or a polypeptide.

1,4-butanedioldiglycidyl ether is reacted with the glycol, suitably PEG in the presence of an alkali and a reducing agent such as sodium borohydride. The reaction takes place at room temperature and yields the desired PEG ether with an oxirane group at the end of the side chain. This oxirane group reacts with a free amino group to form a C—N linkage, on the polypeptide to yield a protected peptide having the partial structure

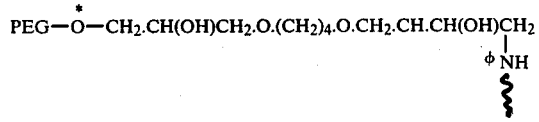

The carboxyamino or thiocarbonylamino benzyl linkage between the terminal oxygen of the glycol such as PEG and a nitrogen of a free amino group on the polypeptide is prepared from the p-amino-benzyl ether of the glycol. The p-amino benzyl ether is treated with phosgene or thiophosgene to yield the corresponding amino acid chloride (or amino thioacid chloride) which is then reacted with the free amino group of a polypeptide, to yield a protected peptide having the partial structure

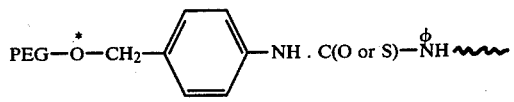

The 2-(hydroxy-3-carboxy)propyl linkage group, which is attached to the terminal oxygen of the glycol at the 2 position of the propyl group.

1,3-O-isopropylidene 2-bromo propane-1,3-diol is reacted with the glycol, say PEG in anhydrous medium in the presence of a base, suitably an alkali, preferably with heating. The resulting 2-glyceryl glycol ether is treated with cyanogen bromide at high pH and low temperature. The polypeptide is added thereto and the coupling occurs to leave the above group between the terminal oxygen of the glycol and a nitrogen of a primary amine group on the polypeptide, to yield a protected peptide having the partial structure

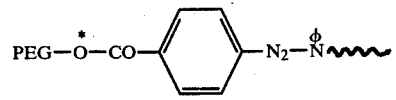

Also available is the anthranilate moiety. In this modification the glycol is again taken up in a reaction inert solvent and treated with isatoic anhydride to yield the anthranilate ester which is used without further purification in the next stage which comprises diazotization. The diazotization is carried out in the usual manner, for example, the anthranilate ester is taken up in water, the solution acidified, suitably with glacial acetic acid, cooled, and sodium nitrite added thereto. The diazonium salt thus formed is available for reaction with polypeptides.

An interesting alternative modification using azido groups involves the photochemical attachment of an azide coupling group. For example, the glycol in a buffer is treated with 4-fluoro-3-nitrophenylazide, the unreacted azide is then removed, suitably by dialysis.

The enzyme in question, for example lysozyme, is taken up in water, treated with the reagent and again, irradiated, suitably at reduced temperatures to yield, for example, PEG-2-nitrophenyl-lysozyme.

In the foregoing discussion, the carbon atom of the polymer to which the coupling moiety is attached is the carbon bearing the terminal hydroxy group. In the case of, say, PPG and PEG, two terminal hydroxy groups are present per moiety. Thus, the possibility exists of cross linking between the polypeptide moieties. Such cross linking is undesirable but may be readily avoided.

One method of cross linking avoidance is to carry out the reactions using a large excess of polymer either at the stage of combination with the coupling moiety or at the coupling state itself.

Alternatively, and preferably, one end of the polymer is pre-blocked. Such polymers, for example, alkylated PEGs such as methoxy polyethelene glycol (MPEG), are commercially available. Such polymers, of course, have only one labile group per polymer moiety.

The terminal hydroxy group may be converted into an amino group. In this procedure the polymer is reacted at its terminal hydroxyl group either with a sulfonating agent such as toluene sulfonyl chloride or with a halogenating agent such as triphenyl phosphine in carbon tetrachloride or triphenyl phosphine and a suitable N-halosuccimide. The thus produced halide or tosylate is then treated with sodium azide and reduced with lithium aluminum hydride to give the corresponding terminal amino compound.

The polymer bearing the terminal amino group is then coupled with a carboxy group of the polypeptide using methods well known in the art. The use of a water soluble carbodiimide such as 1-cyclohexyl-3-(2-morpholino ethyl) carbodiimide, metho-p-toluene sulfonate being especially preferred. There is thus produced an amido linkage comprising the nitrogen of the polymer and the appropriate carbonyl group of the peptide of the general structure

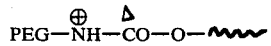

In place of direct coupling of the amino group to form an amido linkage with the polypeptide, the coupling may take place via a maleimide group. In this modification ω-amino PEG is reacted with maleic anhydride and the resultant N-PEG-maleimide reacted with the desired polypeptide yield a protected peptide of the structure

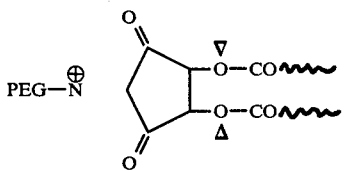

Hereinabove

is the terminal nitrogen on the polymer moiety where the terminal hydroxyl has been replaced by a primary amino group.

Hereinafter the suffix number (i.e., PEG 750) signifies the molecular weight in daltons of the polymer in question.

In an especially preferred embodiment of this invention, alkoxy, suitably methoxy polyethylene glycols, have been attached covalently to the polypeptides.

EXPERIMENTAL

SOURCES OF MATERIALS

Trinitrobenzene sulfonic acid was purchased from Nutritional Biochemicals Company. Cyanuric chloride (2,4,6-trichloro-s-triazine) was obtained from Aldrich Chemicals and was recrystallized twice from benzene immediately before use. Methoxy polyethylene glycols of 1900 and 5000 daltons (MPEG-1900 and MPEG-5000) were supplied by Union Carbide

PREPARATION I

Preparation of 2-O-Methoxy Polyethylene Glycol-4,6-dichloro-s-triazine ("Activated MPEG")

Cyanuric chloride (5.5 g; 0.03 mole) was dissolved in 400 ml anhydrous benzene containing 10 g anhydrous sodium carbonate. MPEG-1900 (19 g; 0.01 mole) was added and the mixture was stirred overnight at room temperature. The solution was filtered, and 1600 ml petroleum ether (boiling range, 35° C.–60° C.) was added slowly with stirring. The finely divided precipitate was collected on a filter and redissolved in 400 ml benzene. The precipitation and filtration process was repeated several times until the petroleum ether was free of residual cyanuric chloride as determined by high pressure liquid chromatography on a column of 5 μm "LiChrosorb" (E. Merck), 250×3.2 mm, developed with hexane, and detected with an ultraviolet detector. Titration of activated MPEG-1900 with silver nitrate after overnight hydrolysis in aqueous buffer at pH 10.0, room temperature, gave a value of 1.7 moles of chloride liberated per mole of MPEG.

In accordance with the above procedure but, where in place of MPEG-1900, MPEG 5000 is used, activated MPEG-5000 was similarly prepared using a 1:3 molar ratio of MPEG and cyanuric chloride.

EXAMPLE I

Urate: Oxygen Oxidoreductase (Uricase) (1.7.3.3)-PEG-Carbomethyl Conjugate (a) Preparation of PEG (i) Preparation of PEG-Methyl Carbomethoxy Ester PEG 750 (2.0 g) is dissolved in liquid ammonia (30 ml.) and the solution treated with sodium until the blue color persists for 5 minutes. The ammonia is allowed to evaporate on a stream of dry nitrogen. The residue is treated with methyl chloroacetate (5 ml.) and the mixture allowed to stand overnight at room temperature and finally heated to 100° for 1 hour. The excess reagent is removed under reduced pressure to provide PEG-methyl carbomethoxy ester.

(ii) Preparation of PEG-Methoxy carbohydrazide

PEG-methyl carbomethoxy ester (2.0 g), methanol (300 ml.) and hydrazine hydrate (15 ml.) are refluxed overnight and the solution is evaporated under reduced pressure to yield PEG-methoxy carbohydrazide.

(iii) Preparation of PEG-Carboxymethyl Azide

The above hydrazide (1.0 g) is dissolved in 2% hydrochloric acid (150 ml.) and 5% sodium nitrite solution (9 ml.), slowly added with stirring and allowed to stand for 20 minutes at room temperature to yield a solution of PEG-carboxymethyl azide which is used in the coupling stage.

(b) Coupling of Urate: Oxygen Oxidoreductase with PEG-Carboxymethyl Azide

The solution containing the azide (16 ml., as produced in part (iii) supra) is adjusted to pH 8.7 by the addition of sodium phosphate. Uricase (25 mg) is added and the solution is stirred for 2 hours at room temperature. The solution is dialyzed and the modified enzyme isolated by chromatography on Sephadex G-50. If desired lyophilization yields the protected enzyme in dry form.

In accordance with the foregoing procedures, but utilizing asparaginase or insulin in place of uricase there is obtained the corresponding PEG-asparaginase or PEG-insulin conjugate. Similarly, there may be used PPG in place of PEG to provide the corresponding PPG-uricase and asparaginase conjugates.

EXAMPLE II

Hydrogen Peroxide: Hydrogen-Peroxide Oxidoreductase (1.11.1.6; "Catalase")-2-PEG-4-Hydroxy-1,3,5-Triazin-6-yl Conjugate (a) Preparation of PEG-4-hydroxy-6-chloro-1,3,5-triazine PEG 750 (30 g., 0.04 mole) or PEG 2,000 (80 g., 0.04 mole) is dissolved in 150 ml. anhydrous benzene containing 8 g. $Na_2CO_3$. The solution is cooled to 10° and cyanuric chloride (7.38 g., 0.04 mole) is added. The solution is stirred overnight at 10°. Water (5 ml.) is added, and the solution then is brought to room temperature for several hours, followed by heating at 40° overnight. Insoluble material is centrifuged off, and solvent is removed by reduced pressure in a rotary evaporator at 40°. A small amount of precipitate which sometimes appears during concentration is removed by the addition of a small amount of benzene to lower the viscosity, followed by centrifugation and reconcentration. The PEG-4-hydroxy-6-chloro-1,3,5-triazine, a viscous liquid at 40°, is stored in the freezer.

(b) Preparation of PEG-HTA-Catalase Conjugate

Catalase (60 mg.; $8.7 \times 10^{-7}$ moles) is dissolved in 3 ml. 0.05 M borate buffer, pH 9.0. PEG 750 (470 mg) is added. After 3 hours the pH is readjusted to 9.0 with sodium hydroxide and the solution left at room temperature overnight. The pH is again adjusted to 9.0. Unreacted PEG is removed by passing the solution through a column of Sephadex G-50. The PEG-HTA-catalase conjugate is concentrated on a rotary evaporator to 1 mg. protein/ml. and stored in the freezer. HTA ≡ -4-hydroxy-1,3,5-triazin-6-yl).

In accordance with the foregoing procedure, but using Carbowax 2000 a similar coupled product is obtained. Similarly, in accordance with the above procedure, but in place of catalase, D-Xylose ketol isomerase (xylose isomerase) or insulin is used, there are obtained the corresponding PEG-HTA-xylose isomerase and PEG-HTA-insulin conjugates.

EXAMPLE III

Cholesterol, reduced - NADP: Oxygen Oxidoreductase (20-β-hydroxylating) (1.14.1.9; cholesterol 20-hydroxylase)-PEG-N-Maleimido Conjugate (a) Formation of N-PEG-maleimide Maleic anhydride (1.0 g., 1/100 mole), benzene (50 ml.) and ω-amino-PEG (1/200 mole) are refluxed for 2 hours. The solution is evaporated under reduced pressure and heated at 200° in a stream of dry nitrogen for 2 hours.

(b) Reaction of N-PEG maleimide with cholesterol 20-hydroxylase

Cholesterol 20-hydroxylase (25 mg) is added to a solution of N-PEG-maleimide (70 mg) in 0.1 M phosphate buffer (pH 7.0, 10 ml.). The solution is allowed to stand at room temperature for 1 hour. The solution is dialyzed and the desired product is isolated from the dialysate by chromatography on Sephadex G-50 to yield a solution of the enzyme-PEG conjugate which may, if desired, be lyophilized.

In accordance with the above procedure, but where in place of cholesterole 20 hydroxylase, insulin is used there is obtained the corresponding PEG-N-maleimido insulin conjugate.

EXAMPLE IV

UDP glucuronate glycuronyltransferase (acceptor unspecific) (2.4.1.17; "UDP glycuronyltransferase") PEG-succinato conjugate (a) Preparation of PEG-dibromo succinate PEG (1.0 g) is dissolved in dry benzene (10 ml.) containing sodium bicarbonate (1.0 g). Dibromo succinic anhydride (0.5 g) is added and the solution stirred overnight. The solution is filtered and the filtrate concentrated under reduced pressure to yield PEG-dibromo succinate.

In accordance with the foregoing procedure, but using diodo succinic anhydride in place of dibromo succinic anhydride, there is obtained the corresponding PEG-diodo succinate.

(b) PEG succinato UDP Glucuronyl transferase

UDP glucuronyl transferase (50 mg) in buffer solution (10 ml., pH 7.0) is slowly treated with PEG-dibromo succinate (100 mg) in water (5 ml) at room temperature. The pH is maintained between 7–8. The desired PEG-enzyme conjugate is isolated by chromatography, on Sephadex G-50. If desired, the product may be isolated by lyophilization.

In accordance with the foregoing procedure but where in place of UDP glucuronyltransferase there is used insulin, there is obtained PEG succinato insulin.

EXAMPLE V

UDP Glucose: α-D-galactose-1-phosphate uridylytransferase (2.7.7.12) (UDP-GPU-transferase)-PEG-anthranilate conjugate (a) Preparation of PEG anthranilate ester PEG (1.0 g) is dissolved in dry benzene (10 ml.) containing sodium bicarbonate (1.0 g). Isatoic anhydride (0.25 g) is added and the solution stirred overnight. The solution is filtered and the filtrate evaporated at 40° C. under reduced pressure to yield PEG-anthranilate ester which is used in the next step without further purification.

(i) Preparation of PEG anthranilate ester diazonium salt

The PEG-anthranilate ester produced as above is dissolved in water (5.0 ml.) and glacial acetic acid (0.5 ml.) added, the solution is cooled to 0°–2° and a concentrated solution of sodium nitrite added dropwise with stirring. Addition of sodium nitrite is stopped when nitrous acid is present.

(b) Coupling of UDP glucose: α-D-galactose-1-phosphate uridylyltransferase with PEG-anthranilate ester diazonium salt UDP-GPU transferase (25 mg) is dissolved in buffer solution (5 ml., pH 7–7.5) and the solution cooled to 0°–2°. This solution is added dropwise to the diazotized solution prepared as above. The pH is maintained at 7–7.5. After 2 hours, the solution is allowed to come to room temperature and filtered and the desired compound is isolated by Sephadex chromatography. If desired, the conjugate may be isolated in solid form by lyophilization.

In accordance with the above procedure but where in place of UDP-GPU transferase there is employed insulin, the corresponding insulin - PEG anthranilate ester is obtained.

EXAMPLE VI

Mucopeptide N-acetylmuramylhydrolase (3.2.1.17)-4-azido-2-nitro-phenyl PEG

(a) 4-azido-2-nitrophenyl PEG

PEG (1.0 g) is dissolved in borate buffer, pH 9.8 (100 ml.) and the solution treated with 4-fluoro-3-nitrophenyl azide (1.0 g) in acetone (10 ml.). The reaction mixture is stirred at 40° overnight and filtered. The filtrate is dialyzed against water, filtered and freeze dried.

(b) Photochemical linkage of lysozyme with 4-azido-2-nitrophenyl PEG

Lysozyme (60 mg) is dissolved in 3 ml. of water and 4-azido-2-nitrophenyl PEG (50 mg) added. The solution was irradiated for 18 hours at 40° C. with two 125 W tungsten lamps immersed in a solution of sodium nitrite (to remove any radiation of shorter wave length than 400 nm.). The preparation was purified by chromatography on Sephadex G-50 to yield PEG-2-nitrophenyl-lysozyme conjugate upon elution. If desired, the solid conjugate may be isolated by lyophilization.

In accordance with the above procedures but where in place of lysozyme there is used insulin, there is obtained PEG-2-nitrophenyl insulin.

EXAMPLE VII

Trypsin-PEG amide conjugate $\omega$-Amino-PEG (see Example VIII) (100 mg) is dissolved in buffer (10 ml. pH 6.0). Trypsin (50 mg) is added, followed by ethyldimethylaminopropyl carbodiimide (200 mg). The pH is maintained at 6. After 1 hour the reaction is stopped by the addition of excess acetate buffer, pH 6. The conjugate is isolated by chromatography on Sephadex G-50.

In accordance with the foregoing procedure, but where, in place of trypsin there are utilized L-citrullin-L-aspartateligase (AMP) or insulin, there is obtained L-citrullin-L-aspartateligase (AMP) (6.3.4.5)-PEG amide conjugate or insulin PEG-amide conjugate.

EXAMPLE VIII

Preparation of $\omega$-Amino PEG

(a) Method (i) Tosylation

PEG (mol.wt. 6000) (50 g) is dissolved in toluene (400 ml.). Toluene (60 ml.) is distilled from the mixture to remove traces of moisture. The solution is cooled and anhydrouse triethylamine (5.5 ml.) is added, followed by p-toluene sulfonyl chloride (3.4 g). The solution is kept overnight at room temperature and then filtered. The filtrate is cooled to 5° and the precipitate is collected. The polymer is dissolved in absolute ethanol (200 ml.) and sodium azide (1.0 g) is added. The solution is boiled under reflux for 36 hours to yield PEG$\omega$-azide.

Method (ii) halogenation

The foregoing procedure for PEG-tosylate is utilized except that thionyl bromide (2.5 ml.) is used instead of p-toluene sulfonyl chloride. The solution is refluxed for 15 minutes after the thionyl bromide to yield PEG-$\omega$ bromide which in turn is similarly converted into PEG-$\omega$-azide.

(b) Conversion to $\omega$-amino PEG

To the ethanolic solution of the $\omega$-azido PEG, Adams catalyst is added and the solution treated with hydrogen until no more hydrogen is taken up. The solution is filtered and concentrated under reduced pressure to a small volume. Dry ether (150 ml.) is added and the polymer allowed to precipitate at 3° overnight. The polymer is collected by filtration.

EXAMPLE IX

Fructose-1,6-diphosphate D-glyceraldehyde-3-phosphatelyase (4.1.2.12; "aldolase")-PEG amide The enzyme (30 mg) is dissolved in 2 M sodium acetate (3 ml.), 0.1 M sodium glyoxylate (1.5 ml.) and 10 MM copper sulfate (1 ml.) Enough 0.4 M acetic acid is added to bring the pH to 5.5. The solution is kept at 20° for 1 hour. The modified protein is isolated by gel filtration on Sephadex. The modified protein is incubated with 2 M sodium acetate (3 ml.) and 2 M acetic acid (1 ml.) and $\omega$-amino-PEG (100 mg) at 37° overnight. The desired product is isolated by chromatography on Sephadex G-50.

EXAMPLE X

Insulin PEG-4-Hydroxy-1,3,5-Triazin-6-yl Conjugate

(a) Preparation of PEG-4-hydroxy-6-chloro-1,3,5-triazine

PEG 750 (30 g., 0.04 mole) or PEG 2,000 (80 g., 0.04 mole) is dissolved in 150 ml. anhydrous benzene containing 8 g. Na$_2$CO$_3$. The solution is cooled to 10° and cyanuric chloride (7.38 g., 0.04 mole) is added. The solution is stirred overnight at 10°. Water (5 ml.) is added, and the solution then is brought to room temperature for several hours, followed by heating at 40° overnight. Insoluble material is centrifuged off, and the solvent is removed by reduced pressure in a rotary evaporator at 40°. A small amount of precipitate which sometimes appears during concentration is removed by the addition of a small amount of benzene to lower the viscosity, followed by centrifugation and reconcentration. The PEG-3-hydroxy-6-chloro-1,3,5-triazine, a viscous liquid at 40°, is stored in the freezer.

(b) Preparation of PEG-HTA-Insulin Conjugate

Insulin 10 mg. i.u. is dissolved in 1 ml. 0.1 M borate buffer, pH 9.2. PEG-HTA 2,000 (179 mg) is added. After 2 hours unreacted PEG-HTA is removed by passing the solution through a column of Sephadex G-10 and adjusted. The PEG-HTA-insulin conjugate is concentrated on a rotary evaporator to protein/ml. and stored in the freezer. (HTA=-4-hydroxy-1,3,5-triazin-6-yl).

In accordance with the foregoing procedure, but using PEG-750, a similar product is obtained.

In accordance with the foregoing procedure, but carrying out the reaction at pH 8.5 and at pH 10, similar products were obtained.

In accordance with the above procedure but where, in place of insulin there are used other peptide hormones including ACTH, Glucagon, Somatostatin, Somatotropin, Thymosin, Parathyroid hormone, Pigmentary hormones, Somatomedin, Erythropoietin, Luteinizing hormone, Chorionic gonadotropin, Hypothalmic releasing factors, Antidiuretic hormones, Thyroid stimulating hormone and Prolactin.

EXAMPLE XI

O-PEG-(P-azo insulin benzyl)ether (a) Formation of O-PEG-p-amino benzyl ether p-Nitrobenzyl chloride (3.46 g, 1/50 mole), powdered sodium hydroxide (2.0 g), anhydrous tetrahydrofuran (20 ml) and PEG (1/100 mole) are refluxed for 3 hours. The solution is filtered and evaporated under reduced pressure and PEG-p-nitronenzyl ether is precipitated by the addition of petroleum ether (bp 30°-40°). The nitro ether is reduced with hydrogen at atmospheric pressure in the presence of Raney nickel catalyst (approx. 1 g) in ethanol (50 ml). The catalyst is removed and the filtrate evaporated to give the title compound.

(b) Coupling with Insulin

O-PEG-p-aminophenyl ether is diazotized in aqueous solution at 0° with nitrous acid. To the purified diazotized solution insulin solution (0.25%) is added and the mixture is kept at 0° for 2 hours. The solution is dialysed at 5°-10° to yield the desired product.

In accordance with the above procedure, but using glucose oxidase (1.1.3.4) in place of insulin, there is obtained the corresponding O-PEG(p-azoglucose oxidase benzyl) ether.

EXAMPLE XII

O-PEG-[p-azo insulin-(2-hydroxy propyloxy)phenyl]ether (a) 3(p-Amino-Phenyloxy)-2-hydroxypropyl ether of PEG PEG (10 g) is treated at 50° with aliquots (20 ml) of 10% aqueous glycidyl p-nitrophenyl ether and with portions (10 ml) of 10% aqueous sodium hydoxide. After 36 hours the solution is neutralized with 2 N acetic acid and evaporated. The PEG ether is extracted from the residue with benzene and precipitated by the addition of excess petroleum ether (bp 30-40).

(b) Coupling with Insulin

The PEG ether is reduced with a solution of titanous chloride (5%) in hydrochloric acid (6 N, 200 ml) for 5 min. at 100°. The solution evaporated at low temperature and the amino ether extracted with acetone and the ether precipitated with excess petroleum ether.

The PEG amino ether derivative (100 mg) in hydrochloric acid (5 ml, 2 N), is cooled to 0° and sodium nitrite solution (2%) added. The pH is adjuted to 7.6-7.7 (phosphate buffer) and aliquots of insulin solution (0.5%) added at 0°. After 18 hours at 0°-5° the solution is dialyzed to yield the desired product. In accordance with the foregoing procedures but using amglase in place of insulin, there is obtained the corresponding O-PEG[azo-α-amylase-(2-hydroxy propyloxy)phenyl] ether.

EXAMPLE XIII

O-PEG Methyl carboxy Insulin (a) Activation of PEG

To a solution of O-PEG-methyl carbomethoxy ether (Ex. 1) (1.0 g) in water (10 ml) is added dropwise a solution of 1.0 g of N-ethoxycarbonyl-2-ethoxy 1,2-dihydroquinoline (EEDQ) in 10% acetone (10 ml.). The pH is maintained at 7.0. After 30 minutes, the pH is adjusted to 1.0 with concentrated hydrochloric acid and is maintained at this pH for 90 seconds to destroy excess EEDQ. The solution is then adjusted to pH 8.

(b) Coupling to Insulin

Insulin (50 mg) in phosphate buffer (pH 8.0) was added to the solution of the activated PEG at 4°-5°. After ½ hour the solution was dialyzed against water to yield the desired product.

In accordance with the above procedure but using urease (3.5.1.5) in place of insulin, there is obtained the corresponding O-PEG methylcarboxy urease.

EXAMPLE XIV

2-O-PEG-1-Hydroxy-3-carboxy Insulin propane (a) 2-Glycerol ether of PEG

PEG (10 g) and 1,3-O-isopropylidene-2-bromo-propane-1,3-diol (10 g), powdered sodium hydroxide (15 g) are heated with stirring in tetrahydrofuran (50 ml) for 3 hours. The solution is filtered and evaporated. The residue is dissolved in 0.1 N hydrochloric acid and the solution allowed to stand at room temperature overnight. The solution is neturalized and evaporated. The PEG ether is taken up in acetone and precipitated by the addition of excess petroleum ether.

(b) Coupling with Insulin

The 2-glycerol ether of PEG (200 mg) is treated with cyanogen bromide (4 ml. 0.5 M) at pH 11.5 at 0°-5° for 8 minutes. Insulin (10 mg) in 0.1 M NaHCO$_3$ is added to the above solution and the mixture is stirred at 4° C. for 24 hours. The solution is dialyzed to yield the desired product.

In accordance with the above procedure but where in place of insulin there is utilized catalase (1.11.1.6) the corresponding 2-O-PEG-hydroxy-3 hydroxy-3 carboxy catalase propane.

EXAMPLE XV

1-(Insulin-2-hydroxy propoxy)-4-3''-O-PEG-2''-hydroxy propoxy Butane (a) Oxirane ether of PEG PEG (5.0 g), 1,4-butanediol diglycidyl ether (1 ml) and 0.6 M sodium hydroxide (1 ml) solution containing 2 mg of sodium borohydride were stirred at room temperature for 8 hours. The solution was neutralized and evaporated. The residue is extracted with acetone and the PEG ether precipitated by the addition of excess petroleum ether.

(b) Coupling to Insulin

Oxirane-PEG (1.0 g) and trypsin (50 mg) in buffer solution (pH 8.5) were allowed to react at room temperature for 48 hours. The solution was dialyzed to yield the desired product.

In accordance with the above procedure but where in place of insulin there is utilized trypsin (3.4.4.4), there is obtained the corresponding ether.

EXAMPLE XVI p-Insulin carboxy amino benzyl/PEG Ether (a) p-Insulin cyanatobenzyl ether of PEG p-Aminobenzyl ether of PEG (Ex.XI) (100 mg) in phosphate buffer (pH 6.8, 0.5 ml) is stirred at room temperature and phosgene solution (10%, 1 ml) carbon tetrachloride added over a period of 1 hour. The carbon tetrachloride is removed under vacuum and the pH of the solution adjusted to pH 8.5.

(b) Coupling to Insulin

Insulin (1.5% in borate buffer (pH 8.5) is added to the above solution and the mixture is stirred for 18 hours at 0°–5°. The solution is dialyzed against water to yield the desired product.

Note the thiophosgene may be substituted for phosgene. This will give the corresponding thiocarbonyl derivative.

In accordance with the above procedure but where in place of insulin there is used ACTH, the corresponding P-ACTH carboxy or thiocarbonyl amino benzyl PEG ether is produced.

EXAMPLE XVII

The procedures of Examples I and III through XVI are carried out in the same manner except that in place of PEG tjere are utilized methoxy polyethylene glycols of 1,900 and 5,000 daltons (MPEG 1900 m MPEG 5000) to give the corresponding MPEG protected product.

EXAMPLE XVIII

In accordance with the procedure of Example II there is utilized activated MPEG prepared in accordance with Preparation I to yield the corresponding MPEG-HTA-polypeptide conjugates.

Enzymatic Activities of PEG-catalase

Catalase—assayed by the method of Beers and Sizer (J. Biol. Chem., 195, 133 (1952)). Both PEG 750-catalase and PEG 2,000-catalase were slightly more active than unmodified catalase:
Unmodified catalase: 41,500 units/mg. protein
PEG 750-catalase: 43,750 units/mg. protein
PEG 2,000-catalase: 43,500 units/mg. protein The heat stabilities of unmodified and PEG 750-catalase were similar at 37° and 60°.

Antigentic Testing of PEG-catalase

Immunization - New Zealand, white adult female rabbits were immunized by the intravenous route with a 1.5 mg/ml. stock solution of beef liver catalase for a period of 4 weeks by which time it received a total of 55 mg. of catalase. Rabbits were bled by cardiac puncture 7 and 14 days after completion of the immunization schedule. Approximately 1 month later, rabbits were injected with 5 mg. of the appropriate antigen and bled by cardiac puncture 1 week after receiving the booster injection.

In vivo and In vitro Tests

Following the last bleeding—an area on the back of the rabbits was shaved with electric clippers and residual fur removed with depilatory. The next day rabbits were injected intradermally with 0.1 ml. of the appropriate antigen and borate-buffered saline (diluent) to test for the possible development of immediate—and/or delayed—type hypersensitivities. All animals were observed for skin reactions for a period of 96 hours after injection.

Rabbit antisera obtained after initial or booster immunization were assayed in vitro for precipitating (1) and complement fixing activities (2,3). Each antiserum (undiluted, 1/10, 1/50) was set up in gel diffusion plates (1.0% Noble Agar in physiological saline with 1.0% azide added as preservative) against both catalase and PEG-HTA-catalase solutions (concentrations ranging from 1000γ/ml. to 5γ/ml). Plates were incubated at room temperature for 48 hours and at 4° C. for 3–4 days. Complement fixing activity of the heat inactivated, sheep red blood cell absorbed antisera was determined using the Microtiter Complement-fixation test (Cooke Engineering Co., Alexandria, Virginia). Antisera were run 1:1 and 1:10 dilutions against catalse and PEG-HTA-catalase dilutions ranging from 1000γ/ml. down to 15γ/ml. Plates were read for presence or absence of hemolysis following incubation at 37° C. for 30 minutes.

Intravenous Immunization with Catalase (a) Analysis of Rabbit Antiserum after Immunization with Catalase Gel Diffusion - Antiserum tested undiluted and 1/10 was positive for precipitating antibodies against catalase. Improtantly, when this antiserum, prepared against native enzyme, was tested against the enzyme modified by polyoxyethylene residues there was no evidence of any cross-reactions.

Complement Fixation—Both initial and booster sera were positive for complement-fixing activity when tested against native catalase. When the modified catalase was used as the reacting antigen, the results were negative.

PEG-Insulin Immunoassay

PEG-HTA-Insulin was prepared in accordance with Example II and tested for antigenic activity by the method of

| Sample | (1) Insulin Activity, μ units/ml. (animal assay) | (2) Insulin Antibodies Activity, μ units/ml. (radioimmunoassay) |
|---|---|---|
| Unmodified Insulin | 137 | 127 |
| PEG-HTA Insulin (750) | 72* | 0 |
| PEG-HTA Insulin (2,000) | 90* | 0 |

*These figures are obtained as a dilution figure and are not actual assay figures.

The foregoing results show that PEG-HTA-insulin has no antigenic activity vis a vis insulin antiserum.

PEG-HTA-Insulin Assay

Preliminary insulin and PEG-HTA-insulin containing the same amount of insulin were injected into test rabbits and blood sugar levels measured by the "Glucostat" method (Worthington Biochemical Corporation, Freehold, N. J.).

| After 3 hours | Blood glucose level |
|---|---|
| PEG-HTA Insulin | 50% of normal |

-continued

| After 3 hours | Blood glucose level |
|---|---|
| Insulin | 20% of normal |

These tests indicate that the PEG-HTA-insulin has insulin activity of about 50% of insulin based on weight of conjugated insulin administered.

PEG Insulin Rat Assay

Standard laboratory rats (220/225 g.) were made diabetic by the procedure of Goldner (Bull.-N.Y.Acad.Med. 21, 44, (1945) utilizing alloxan injections. No food was given to the test animals during the test period. Insulin, & PEG 2000-HTA insulin formulations produced at pH 9.2 and 10.5 were administered to the test rats. The pH 10.5 product showed no lowering of blood glucose levels.

The results are tabulated below and summarized in the Figure.

| Time (hrs) | Blood Glucose Level mg/100 ml. | Drop Over Initial Level (mg/100 ml) | % Drop Over Control |
|---|---|---|---|
| Insulin (intramuscularly) | | | |
| 0 | 410 | — | — |
| 1 | 295 | 135 | 32.9 |
| 2 | 270 | 140 | 34.1 |
| 4 | 290 | 120 | 29.2 |
| 6 | 400 | 10 | 02.4 |
| Control (no food during test period) | | | |
| 0 | 520 | 0 | 0 |
| 2 | 510 | 10 | 1.9 |
| 4 | 490 | 30 | 5.7 |
| 6 | 470 | 50 | 9.6 |
| 10 | 395 | 125 | 24.0 |
| PEG HTA Insulin (pH 9.2) (intravenous) | | | |
| 0 | 305 | — | — |
| 2 | 72.5 | 232 | 76.2 |
| 4 | 101.5 | 203.5 | 66.7 |
| *5 | — | — | — |
| 8 | 230 | 75 | 24.6 |

*animals fed after this point.

We claim:
1. A physiologically active, substantially non-immunogenic water soluble polypeptide composition comprising, a physiologically active polypeptide coupled with a coupling agent to
at least one substantially linear polymer having a molecular weight of between about 500 to about 20,000 daltons selected from the group consisting of polyethylene glycol and polypropylene glycol
wherein the polymer is unsubstituted or substituted by alkoxy or alkyl groups, said alkoxy or alkyl group possessing less than 5 carbon atoms.
2. The polypeptide composition of claim 1 wherein the polypeptide is selected from the group consisting of insulin, ACTH, glucagon, somatostatin, somatotropin, thymosin, parathyroid hormone, pigmentary hormones, somatomedin, etythropoietin, luteinizing hormone, chorionic gonadotropin, hypothalmic releasing factors, antidiuretic hormones, thyroid stimulating hormone and prolactin.
3. The polypeptide composition of claim 2 wherein the polypeptide is insulin.
4. The polypeptide composition of claim 1 wherein the polymer has a molecular weight of between about 750 and 2,000 daltons.
5. The polypeptide composition of claim 4 which comprises between 10 and 100 polymer moieties per molecule of insulin.
6. The polypeptide composition of claim 1 wherein the polymer is polyethylene glycol.
7. The polypeptide composition of claim 4 wherein the polypeptide is insulin.
8. The polypeptide composition of claim 6 wherein the polypeptide is insulin.
9. The polypeptide composition of claim 1 wherein the group between the polypeptide and the polymer has the formula selected from the group consisting of

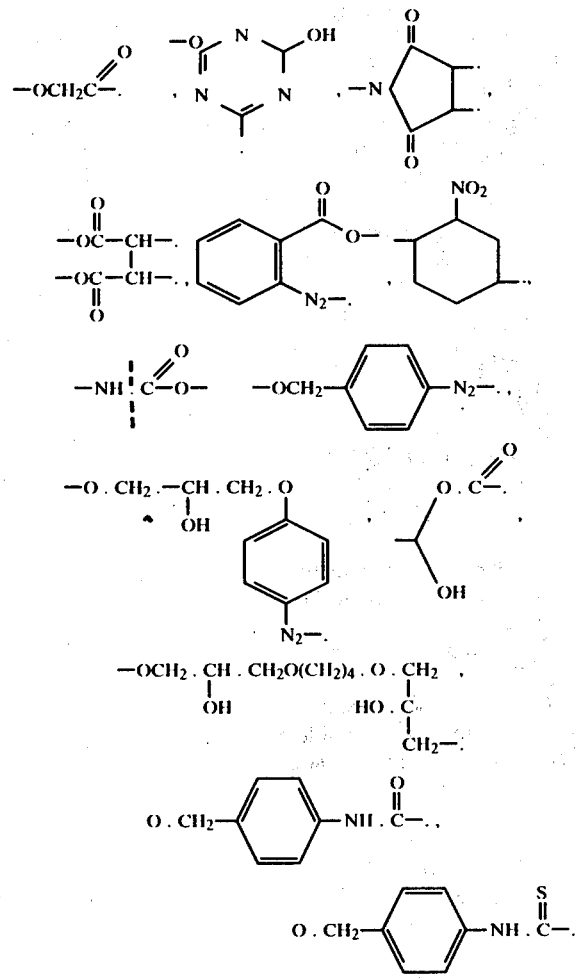

wherein the bond designated—· of each group is attached to the polypeptide provided that in the case where the group is

portion is part of the polypeptide carboxy group.
10. The polypeptide composition of claim 9 wherein the polypeptide is insulin.
11. The polypeptide composition of claim 10 wherein the group is

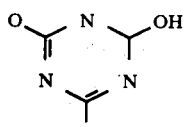

12. The polypeptide composition of claim 11 wherein the polymer is polyethylene glycol.

13. A substantially non-immunogenic insulin-containing composition comprising the insulin composition of claim 3 and a pharmaceutically acceptable injectable carrier.

14. A process of preparing a physiologically active, substantially non-immunogenic water soluble polypeptide composition from a polypeptide; originally having physiological activity and immunogenicity which comprises the steps of:
(a) reacting at least one terminal carbon atom bearing a hydroxy group, of a substantially straight chain polymer selected from the group consisting of polyethylene glycol and polypropylene glycol having a molecular weight of from about 500 to about 20,000 daltons said polymer being unsubstituted or substituted by alkoxy or alkyl groups, said alkoxy or alkyl groups having less than 5 carbon atoms with a coupling agent to provide an activated polymer containing a reactive terminal group, and;
(b) reacting a physiologically active immunogenic poly peptide with from 10 to 100 moles of said activated polymer per mole of poly peptide by coupling said polypeptide to the reactive terminal group of the polymer to provide said water soluble polypeptide composition.

15. A process of claim 14 wherein the coupling agent is cyanuric chloride.

16. A process of claim 15 wherein the polypeptide is insulin.

17. A physiologically active substantially non-immunogenic water soluble enzyme composition comprising a physiologically active enzyme coupled with a coupling agent to
at least one substantially linear polymer selected from the group consisting of polyethylene glycol and polypropylene glycol having molecular weight of between 500 and 20,000 daltons
wherein the polymer moiety is unsubstituted or substituted by alkoxy or alkyl groups, said alkoxy or alkyl group possessing less than 5 carbon atoms.

18. The enzyme composition of claim 17 wherein the polymer has a molecular weight of between about 500 and about 5,000 daltons.

19. The enzyme composition of claim 17 which comprises between 10 and 100 polymer moieties per molecule of enzyme.

20. The enzyme composition of claim 17 wherein the polymer is polyethylene glycol.

21. The enzyme composition of claim 17 wherein the enzyme is selected from the group consisting of oxidoreductases, transferases, hydrolases, lyases, isomerases, and ligases.

22. The enzyme composition of claim 17 wherein the group between the enzyme and the polymer has the formula selected from the group consisting of

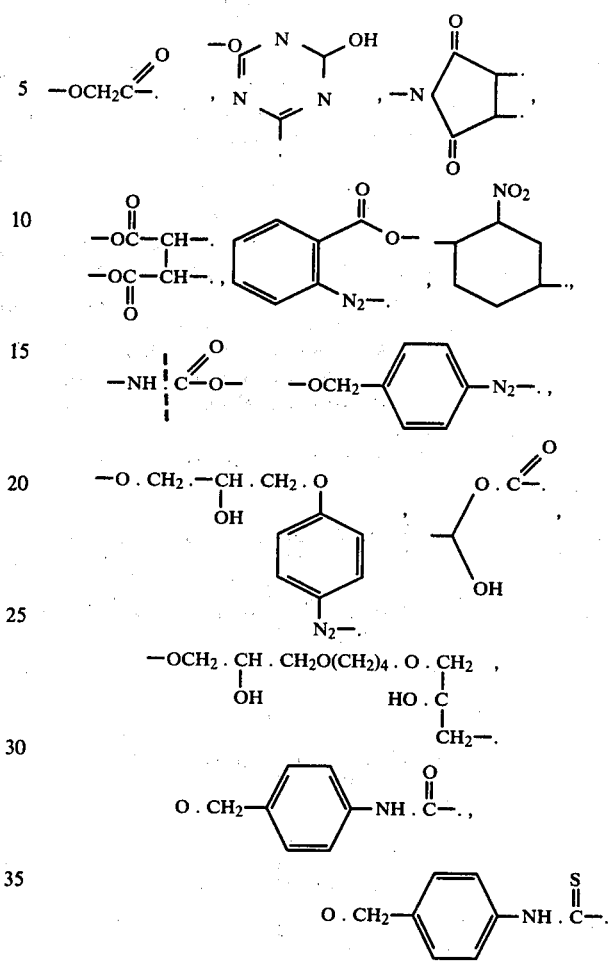

wherein the bonds designated —· of each group is attached to the enzyme provided that in the case where the group is

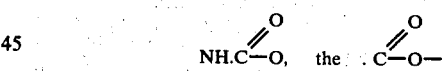

portion is part of the polypeptide carboxy group.

23. A process of preparing a physiologically active, substantially non-immunogenic water soluble enzyme composition from an enzyme originally having physiological activity and immunogenicity which comprises the steps of:
(a) reacting at least one terminal carbon atom bearing a hydroxy group, of a substantially straight chain polymer selected from the group consisting of polyethylene glycol and polypropylene glycol having a molecular weight of from about 500 to about 20,000 daltons said polymer being unsubstituted or substituted by alkoxy or alkyl groups, said alkoxy or alkyl groups having less than 5 carbon atoms with a coupling agent to provide an activated polymer containing a reactive terminal group, and
(b) reacting a physiologically active immunogenic enzyme with from 10 to 100 moles of said activated polymer per mole of enzyme by coupling the enzyme to the reactive terminal group of said polymer to provide said water soluble enzyme composition.

24. The process of claim 23 wherein the enzyme is selected from the group consisting of oxidoreductases, transrerases, hydrolases, lysases, isomerases, and ligases.

25. A process of claim 24 wherein the coupling moiety is cyanuric chloride.

26. A process of claim 24 wherein the polymer is polyethylene glycol.

27. A process of claim 26 wherein the coupling moiety is cyanuric chloride.

* * * * *